United States Patent [19]

Lee et al.

[11] Patent Number: 5,022,259

[45] Date of Patent: Jun. 11, 1991

[54] AUTOMATED VAPOUR PRESSURE ANALYZER

[76] Inventors: William L. Lee, P.O. Box 519, Bruderheim, Alberta T0B-0S0; Alexander McLean, 152 Garland Crescent, Sherwood Park, Alberta T8A-2R6; Ronald E. Daye, 1619 Cayuga Dr. N.W., Calgary, Alberta T2L0N2, all of Canada

[21] Appl. No.: 511,758

[22] Filed: Apr. 20, 1990

[51] Int. Cl.$^5$ .............................................. G01N 7/16
[52] U.S. Cl. .................................................. 73/64.20
[58] Field of Search ...................... 73/64.2, 61.3, 29.01

[56] References Cited

U.S. PATENT DOCUMENTS

| | | | |
|---|---|---|---|
| 3,901,062 | 8/1975 | Lynch et al. | 73/64.2 |
| 4,332,159 | 6/1982 | Chin et al. | 73/64.2 |
| 4,522,056 | 6/1985 | Chin et al. | 73/64.2 |
| 4,578,151 | 3/1986 | Soderstrom, III et al. | 73/64.2 X |
| 4,667,508 | 5/1987 | Soderstrom, III et al. | 73/64.2 |
| 4,905,505 | 3/1990 | Reed | 73/64.2 |

*Primary Examiner*—Hezron E. Williams
*Assistant Examiner*—Joseph W. Roskos
*Attorney, Agent, or Firm*—George Haining Dunsmuir

[57] ABSTRACT

An automated vapor pressure measuring apparatus includes an elongated cylindrical casing with a valve therein separating a liquid sample receiving chamber (the liquid chamber) from a vapor decompression chamber (vapor chamber), heaters for heating the chambers separately, temperature probes extending into both chambers, a pressure measuring device connected to the vapor chamber, a device to rotate the cylindrical casing to effect mixing of the contents and a programmable controller for controlling operation of the valve between the chambers, the heaters, valves for introducing and discharging liquid sample from the liquid chamber, and a valve for discharging vapor from the vapor chamber, for monitoring the temperature probes and the pressure measuring device, for controlling the rotating device and for providing visual indications of temperature and pressure.

10 Claims, 1 Drawing Sheet

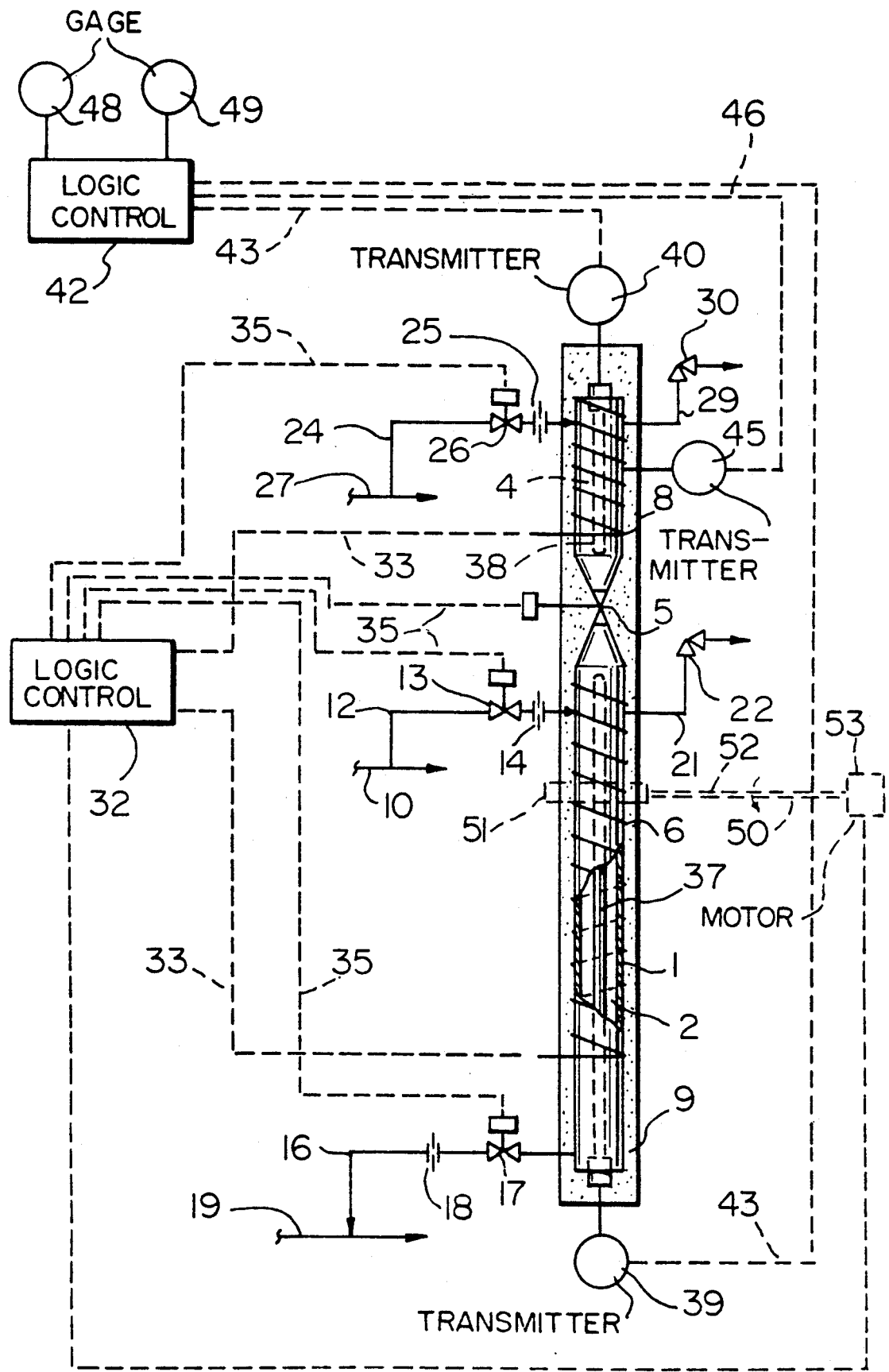

5,022,259

AUTOMATED VAPOUR PRESSURE ANALYZER

BACKGROUND OF THE INVENTION

This invention relates to a vapor pressure measuring apparatus.

While the apparatus of the present invention was designed specifically for measuring the vapor pressure of liquid hydrocarbons, it will be appreciated that the apparatus can be used to measure the vapor pressure of a wide variety of liquids, both hydrocarbon and non-hydrocarbon. The analyzer may be used to determine liquid Reid vapor pressure in "gage" or "absolute" units for hydrocarbon liquids as defined in procedure ANSI/ASTM D 1269-79 and vapor pressure of hydrocarbon liquid defined in procedure ANSI/ASTM D 323-79, respectively. Depending on inlet conditions such as pressure and temperature of a sample, the analyzer will measure vapor pressure over a wide range of temperatures thus determining a vapor pressure curve for each sample. The analyzer is intended for operation on a batch basis with time cycles typically in the range of one to three minutes, and can produce repeatable results within the accuracy specified by the above mentioned ANSI/ASTM procedures.

At present, the above mentioned ANSI/ASTM laboratory procedures are commonly used to measure Reid vapor pressure of petroleum products. Both methods are laboratory procedures which require the performance of specific steps to produce predictably accurate results. Both methods require careful handling of samples, preconditioning of sample containers, heat bath systems, and agitation of samples during an approximate thirty minute time period to ensure mixing and vapor separation. The ANSI/ASTM D 323-79 procedure requires an air chamber to be preheated to 100° F. before sampling.

In the past, a variety of methods of measuring vapor pressures have been proposed, including the use of an apparatus consisting of a temperature control bath, a continuous sampling device and two positive displacement pumps of different capacities to cause vapor separation. Vapor pressure is measured in a chamber, the temperature of which is controlled by a bath at 100° F. The device was designed primarily for measuring the vapor pressure of crude oil. In accordance with another method, the vapor pressure of blended gasoline products has been determined by measuring the temperature drop produced by the expansion of a liquid sample from a high to a low pressure under substantially adiabatic conditions. In order to improve accuracy, methods have been devised to remove accumulated fixed gases in the apparatus. Finally, vapor pressure has been measured using an apparatus including a temperature control bath and two sample pumps of different capacities. In essence, a sample is continuously vaporized across an orifice plate into a chamber. The vapor pressure is measured in the chamber by a bellows-type pressure gage employing a Wheatstone Bridge.

The above described methods are reasonably accurate. However, they employ elaborate sampling techniques such as time consuming manual laboratory procedures and the use of two pumps in series to collect samples and ensure vaporization. The laboratory procedure includes special sampling steps and agitation of the liquid to ensure mixing. The continuous sampling device requires a liquid, temperature controlled bath which is difficult to use in industrial applications without special consideration. Bath temperature is difficult to control within ±/1.5° F. accuracy. The continuous device requires varying levels of calibration to a standard before handling liquids of significantly different composition or physical properties. Moreover, the prior art devices cannot provide vapor pressure values over a wide range of temperatures during each sampling cycle.

The object of the present invention is to overcome the above-defined difficulties encountered with prior art devices by providing an automated apparatus which is relatively simple in terms of design, reliability and accuracy, and which can be used to determine the vapor pressure of a wide variety of hydrocarbon and non-hydrocarbon liquids.

Another object of the invention is to provide an apparatus which can be used for precise quality control of liquids in industrial applications, and to provide an apparatus which can be portable for use in remote locations such as pipelines.

An additional object of the invention is to provide an apparatus with a relatively short cycle for providing data of temperature versus vapor pressure for a given liquid.

BRIEF SUMMARY OF THE INVENTION

Accordingly, the present invention relates to an automated vapor pressure measuring apparatus, comprising: casing means defining a first liquid sample chamber and a second vapor decompression chamber; a first valve between said first and second chambers; first inlet means for introducing a liquid sample into said first chamber; first drain means for draining said first and second chambers; heating means for heating said casing means and consequently the contents of said first and second chambers; first probe means for measuring the temperature in said first chamber; second probe means for measuring the temperature in said second chamber; pressure measuring means for measuring the vapor pressure in said first and second chamber; and programmable control means for controlling said first valve, said first inlet means, said first drain means and said heating means, and for monitoring said first and second probe means and said pressure measuring means, whereby automatically to perform the steps of introducing a liquid sample into said first chamber, depressuring liquid sample into said second chamber, heating said sample in said chambers to a predetermined temperature at which vapor pressure is required, measuring the vapor pressure in said first and second chamber, and discharging the vapor-liquid mixture from said chambers to automatically measure vapor pressure of a liquid sample.

The invention further may include means to rotate said casing means to effect mixing of the contents thereof, i.e. the vapor-liquid mixture.

BRIEF DESCRIPTION OF THE DRAWINGS

The invention will be described in greater detail with reference to the accompanying drawing, which illustrates a preferred embodiment of the invention, and wherein the single figure is a schematic flow diagram of an apparatus in accordance with the present invention.

DESCRIPTION OF THE PREFERRED EMBODIMENT(S)

With reference to the drawing, the apparatus of the present invention includes an elongated casing 1, defining a liquid sample chamber 2 and a vapor decompression chamber 4 separated by a valve 5. The casing 1 can, but not necessarily, be formed of ½-¾ inch stainless steel tubing and is generally from one to two feet in total length. A first heating element 6 is enclosed around the portion of the casing 1 defining the chamber 2, and a second heating element 8 is enclosed around the portion of the casing 1 defining the chamber 4. Means can be also provided, as shown schematically at 50, to effectively rotate casing 1, one or more times, to effect efficient mixing of the liquid-vapor mixture contained within casing 1. A suitable structure could include a collar 51, extension shaft 52 and electric motor 53. The sequence of rotation may be manually controlled by means of a switch (not shown), or, as shown, by a programmable logic controller 32. The heating elements 6 and 8 are individually controlled, and the entire casing is wrapped in an insulating material 9.

A liquid sample from a sample line 10 is introduced into the chamber 2 through an inlet duct 12, which contains a valve 13 and a restricted orifice plate 14. When sampling liquids such as propane, the pressure drop across the valve 13 can result in low temperatures which can cause sealing problems and leaking at the valve. Allowing the pressure drop to occur at the plate 14 eliminates valve sealing problems. The sample is drained to atmospheric pressure from the chamber 2 through an outlet duct 16 containing a valve 17 and an orifice plate 18 to a drain line 19. Overpressure in the chamber 2 is released through a line 21 and a pressure relief valve 22. Vapor from the chamber 2 passes through the valve 5 into the chamber 4, and is discharged to atmosphere through a line 24 containing an orifice plate 25 and a valve 26 to vent line 27. Any overpressure in the chamber 4 is released through a line 29 and a pressure relief valve 30. Heating elements 6 and 8 are connected to a programmable logic controller 32 by lines 33, and the valves 5, 13, 17 and 26 are connected to the logic controller 32 by line 35.

The temperature in the chambers 2 and 4 is measured using surface sensitive resistance thermal probes 37 and 38, respectively, which extend out of the casing 1 to transmitters 39 and 40, respectively. The probes 37 and 38 should be of the surface sensitive type and of maximum length in order to maintain optimum accuracy when measuring the temperature of multi-component samples. The ratio of temperature sensing surface area to the volume of the chamber is also a factor in the accurate measurement of the temperature of a multi-component mixture. The transmitters 39 and 40 are connected to a logic controller 42 by lines 43. The vapor pressure in the chamber 4 is measured and transmitted to the logic controller 42 by a pressure transmitter 45 and a line 46. When the valve 5 is opened, and a sample is being heated to determine vapor pressure, the pressure in both of the chambers 2 and 4 is measured by the transmitter 45. Gages 48 and 49 are connected to the logic controller 42 for providing a visual indication of temperature and pressure respectively.

As mentioned above, the temperature in the chambers 2 and 4, and the introduction and discharge of fluid from such chambers are controlled by logic controller 32, and the temperature and pressure in the chambers is monitored by the logic controller 42. The controller 32 is programmed to ensure that the sampling process, timing, valve operating, and casing rotational sequences are properly controlled.

While the logic controllers 32 and 42 are shown as separate devices, in fact, such controls are a single device, i.e. a microprocessor.

The use of the apparatus will be described by means of two specific examples, the first being a determination of the absolute vapor pressure of volatile crude oil and non-viscous petroleum products as defined in procedure ANSI/ASTM D 323-79.

Assuming that sampling has already occurred, the vent valve 26 from the chamber 4, the liquid sample valve 13 and the drain valve 17 are closed, and the valve 5 interconnecting the chambers 2 and 4 is open. In order to drain both chambers 2 and 4, the valves 17 and 26 are opened, the valve 26 being open to atmosphere. The liquid and vapor in both of the chambers 2 and 4 are drained or aspirated to a hydrocarbon drain line 19 at atmospheric pressure. As the sample is drained, air is drawn into the chambers 4 and 2.

After sufficient time has elapsed to permit the sample to be drained and the chamber 4 to be filled with air, and chambers 2 and 4 are both at atmospheric pressure, the drain valve 17 and the valve 5 are closed. Heat is applied to the chamber 4 by means of the element 8 to preheat the vapor decompression chamber to a base temperature at which a vapor pressure measurement is required. Normally the base temperature is 100° F. for determining Reid vapor pressure. The temperature of the vapor decompression chamber 4 is measured by the probe 38 and the transmitter 40. When the temperature in the chamber 4 reaches the required level, heating is terminated and the valve 26 is closed. During operation of the apparatus over an extended period of time, residual heat in the casing 1 and the insulation 9 may provide sufficient heat for the preheat stage. Upon completion of preheating, the vapor decompression chamber 4 is at the base temperature and atmospheric pressure, which counteracts external atmospheric pressure. The net result is that the transmitter 45 can provide an accurate measurement of vapor pressure, equivalent to the absolute vapor pressure, to the logic controller 42 for reading on the gage 49 in gage pressure. The valve 13 is opened, and a liquid sample is used to flush the chamber 2 for several seconds to ensure that the previous sample is thoroughly washed from the sample duct 12 through the outlet duct 16 to the drain line 19. When flushing has been completed, the drain valve 17 is closed to liquid fill the sample chamber 2, and the valve 13 is closed. The liquid sample is isolated in the chamber 2 at sample process conditions. The sample may cool slightly due to pressure drop across the orifice plate 14. For the analyzer to function, the liquid sample from the line 10 must be at a temperature below the required base temperature. Otherwise sample conditioning will be required.

The valve 5 is opened and the vapor in the chamber 4 and the liquid sample in the chamber 2 reach equilibrium at a temperature below the base temperature, and at a pressure below the required vapor pressure. Also sample conditioning may be required if the sample is volume compressible at sample conditions. If, when valve 5 is opened, the liquid sample in chamber 2 expands under decompression into chamber 4, error could be introduced depending on the compressibility of the liquid sample. With the vent valve 26, the sample valve 13 and the drain valve 17 closed and the valve 5 open, the heater 6 is actuated to apply heat to the casing 1 in the area of the chamber 2. The rotating means 50 is actuated to rotate casing 1 by 180°, one or more times to ensure complete mixing of the liquid-vapor mixture. As heat is applied to the liquid sample chamber 2, the temperature rise is monitored by the probes 37 and 38, and pressure increase is monitored by the pressure transmitter 45. When the temperature reaches the base temperature, the pressure is measured and recorded by the logic controller 42 to provide the liquid sample absolute vapor pressure in gage units at the base temperature.

The process can then be repeated starting with the draining step described above.

The same apparatus as described hereinbefore may be used to determine the gage vapor pressure of liquified petroleum gas products as defined in procedure ANSI/ASTM D 1267-79. In this process, the line 24 and the valve 26 are connected to the liquid sampling line 10, and there is no vent to atmosphere. During the sampling step immediately preceding draining, the valves 13 and 26 and 17 are closed, and the valve 5 is opened to interconnect the chambers 2 and 4. In order to drain the chambers, the valve 17 is opened to a hydrocarbon drain line 19. Liquid and vapor in both the chambers 2 and 4 are drained or aspirated to the hydrocarbon drain line 19 at atmospheric pressure.

The liquid sample valves 13 and 26 are open so that liquid samples can flush both chambers 2 and 4 for several seconds to ensure that the previous sample is thoroughly removed through the duct 16 and the line 19.

Following flushing of the chambers 2 and 4, the valves 13 and 26 are closed and both chambers 2 and 4 drain. Upon completion of the flush and drain, the drain valve 17 is closed.

Both chambers are thus isolated in a vapor phase at atmospheric pressure. The valve 5 is closed. The valve 13 is opened to introduce liquid sample into the chamber 2 at liquid sample process conditions. The sample may cool because of the pressure drop across the orifice plate 14. In order for the analyzer to function, the liquid sample must be at a temperature below the required base temperature. Otherwise, sample conditioning will be required.

The valve 5 is opened and the vapor in the chamber 4 reaches equilibrium with the liquid sample in chamber 2 at a temperature below the base temperature and a pressure below the required vapor pressure.

With the sample valves 13 and 26 and the drain valve 17 closed, and the valve 5 open, heat is applied to the chamber 2. The rotating means 50 is again activated, following which, the temperature and pressure in the apparatus is monitored, such that when the temperature reaches the base temperature, the pressure is measured and recorded by the logic controller 42 as the sample gage vapor pressure at the required base temperature. The process can then be repeated starting with the draining step.

The accuracy of the above described apparatus when carrying out the above defined processes has been found to be at least equal to the accuracy set out in procedures ANSI/ASTM D 323-79 and ANSI/ASTM D 1267-79. The apparatus has been tested with a wide variety of liquids over a wide range of vapor pressures, and determined to be ±/1% accurate. Accuracy of the apparatus is at present dependent upon the volume ratio of the vapor decompression chamber 4 to the liquid sample chamber 2, the length to diameter dimension ratio of each chamber, and the rate of heat input. All of these values are variable and dependent upon the physical properties and composition of the liquid being tested.

Both of the processes described herein are carried out on a batch basis.

For industrial use, when the analyzer is to be used to measure vapor pressure of one or more liquids, the apparatus can be permanently mounted in a heated, weather resistant cabinet. The logic control can be mounted either in the cabinet or remotely in a control room. For portable use, the apparatus can be mounted in a metal case which contains the analyzer and the logic controller, requiring a power supply for operation.

What we claim is:

1. An automated vapor pressure measuring apparatus, comprising: casing means defining a first liquid sample chamber and a second vapor decompression chamber; first valve between said first and second chambers; first inlet means for introducing a liquid sample into said first chamber; first drain means for draining said second chamber; purge or atmospheric means for introducing a gas into said first and second chambers; heating means for heating said casing means and consequently the contents of said first and second chambers; first probe means for measuring the temperature in said first chamber; second probe means for measuring the temperature in said second chamber; pressure measuring means for measuring the vapor pressure in said first and second chamber; and programmable control means for controlling said first valve, said first inlet means, said first drain means, said purge or atmospheric means and said heating means, and for monitoring said first and second probe means and said pressure measuring means whereby automatically to perform the steps of introducing a liquid sample into said first chamber, depressuring said liquid sample into said second chamber, heating said sample, measuring the vapor pressure in said first and second chambers, and discharging the vapor-liquid sample from said first and second chambers to automatically measure vapor pressure of a liquid sample.

2. An apparatus according to claim 1, wherein said heating means includes a first heating element for heating said first chamber and a second heating element for heating said second chamber.

3. An apparatus according to claim 1, wherein said first and second temperature probe means include surface sensitive probes extending into said first and second chambers.

4. An apparatus according to claim 1, including a second valve in said first inlet means for controlling the introduction of the liquid sample into said first chamber; and a third valve in said first drain means for controlling the discharging of vapor-liquid mixture from said first and second chambers.

5. An apparatus according to claim 4, including first restricted orifice means in said first inlet means between said second valve and said first chamber; and second restricted orifice means in said first drain means for preventing sealing problems in said second and third valve.

6. An apparatus according to claim 5 including second drain means for draining liquid from said first and second chambers.

7. An apparatus according to claim 6, including a fourth valve in said second drain means; and third restricted orifice means in said second drain means downstream of said fourth valve in the direction of liquid travel for preventing sealing problems in said fourth valve.

8. An apparatus according to claim 1, including transmitter means for transmitting temperature measurements from said first and second probe means to said control means, and pressure measurements from said pressure measuring means to said control means.

9. An apparatus according to claim 1 including pressure release means in said casing means for releasing any overpressure in said first or second chambers.

10. An apparatus according to claim 1, including means to rotate said casing means for mixing the liquid-vapor mixture contained therein.

* * * * *